United States Patent
Achard et al.

(10) Patent No.: US 10,677,763 B2
(45) Date of Patent: *Jun. 9, 2020

(54) METHOD FOR WETTING A SONOTRODE

(71) Applicant: CONSTELLIUM ISSOIRE, Issoire (FR)

(72) Inventors: Jean-Louis Achard, Vizille (FR); Philippe Jarry, Grenoble (FR)

(73) Assignee: CONSTELLIUM ISSOIRE, Issoire (FR)

( * ) Notice: Subject to any disclaimer, the term of this patent is extended or adjusted under 35 U.S.C. 154(b) by 355 days.

This patent is subject to a terminal disclaimer.

(21) Appl. No.: 15/516,629

(22) PCT Filed: Oct. 6, 2015

(86) PCT No.: PCT/FR2015/052679
§ 371 (c)(1),
(2) Date: Apr. 3, 2017

(87) PCT Pub. No.: WO2016/055728
PCT Pub. Date: Apr. 14, 2016

(65) Prior Publication Data
US 2017/0299555 A1    Oct. 19, 2017

(30) Foreign Application Priority Data
Oct. 7, 2014    (FR) ..................... 14 02256

(51) Int. Cl.
*B06B 3/00*    (2006.01)
*G01N 29/34*    (2006.01)
(Continued)

(52) U.S. Cl.
CPC .............. *G01N 29/34* (2013.01); *B06B 3/00* (2013.01); *C22B 9/026* (2013.01); *C22B 21/06* (2013.01);
(Continued)

(58) Field of Classification Search
CPC ........... B06B 3/00; C22B 9/026; C22C 21/04; G01N 2291/022; G01N 29/02;
(Continued)

(56) References Cited

U.S. PATENT DOCUMENTS 3,054,309 A  *  9/1962  Elmore ................ B23K 20/106
228/1.1
4,054,239 A  *  10/1977  Watson, Jr. .......... B23K 1/0012
228/183
(Continued)

FOREIGN PATENT DOCUMENTS

GB    1487203 A    9/1977
JP    2007239102 A    9/2007

OTHER PUBLICATIONS

International Search Report of PCT/FR2015//052679 dated Feb. 2, 2016.

*Primary Examiner* — Jie Yang
(74) *Attorney, Agent, or Firm* — McBee Moore & Vanik IP, LLC

(57) ABSTRACT

The method comprising the following steps:
a) Providing a first bath of a liquid metal (1) comprising aluminium with a content X and magnesium with a content Y, the magnesium content Y being different to zero,
b) Immersing at least partially a sonotrode (3) formed from a material inert to liquid aluminium, in the first bath of liquid metal (1), and
c) Applying power ultrasounds to the sonotrode (3) so as to excite the liquid metal (1) until wetting (5) of the sonotrode (3) by the liquid metal (1) is obtained.
d) Cooling the first liquid metal (1) of the first bath until solidification of the first liquid metal (1) around the sonotrode (3) is obtained, generating an intimate bond (6) between the sonotrode (3) and the solidified first
(Continued)

liquid metal (1) having a bonding strength substantially equal to that of brazing between two metals.

e) Machining the solidified first metal (1) in the form of a flange (7) configured for the attachment of a mechanical amplifier and/or of a transducer (4).

10 Claims, 3 Drawing Sheets

(51) Int. Cl.
    *G01N 33/205*     (2019.01)
    *C22B 9/02*     (2006.01)
    *C22B 21/06*     (2006.01)
    *G01N 29/032*     (2006.01)
    *G01N 29/22*     (2006.01)
    *C22C 21/04*     (2006.01)
    *C22C 21/08*     (2006.01)
    *G01N 29/02*     (2006.01)

(52) U.S. Cl.
    CPC .............. *C22C 21/04* (2013.01); *C22C 21/08* (2013.01); *G01N 29/02* (2013.01); *G01N 29/032* (2013.01); *G01N 29/228* (2013.01); *G01N 33/205* (2019.01); *G01N 2291/022* (2013.01); *Y02P 10/234* (2015.11)

(58) Field of Classification Search
    CPC .... G01N 29/032; G01N 29/228; G01N 29/34; G01N 33/205; Y02P 10/234
    USPC .......................................................... 75/671
    See application file for complete search history.

(56) References Cited

U.S. PATENT DOCUMENTS

| | | | |
|---|---|---|---|
| 5,228,494 A * | 7/1993 | Rohatgi | ................ C22C 1/1036 164/102 |
| 8,652,397 B2 * | 2/2014 | Rundquist | ............ C22B 21/064 266/217 |
| 2012/0042751 A1 | 2/2012 | Rundquist et al. | |
| 2017/0306441 A1 * | 10/2017 | Achard | ................... C22B 21/06 |

* cited by examiner a)

b)

c)

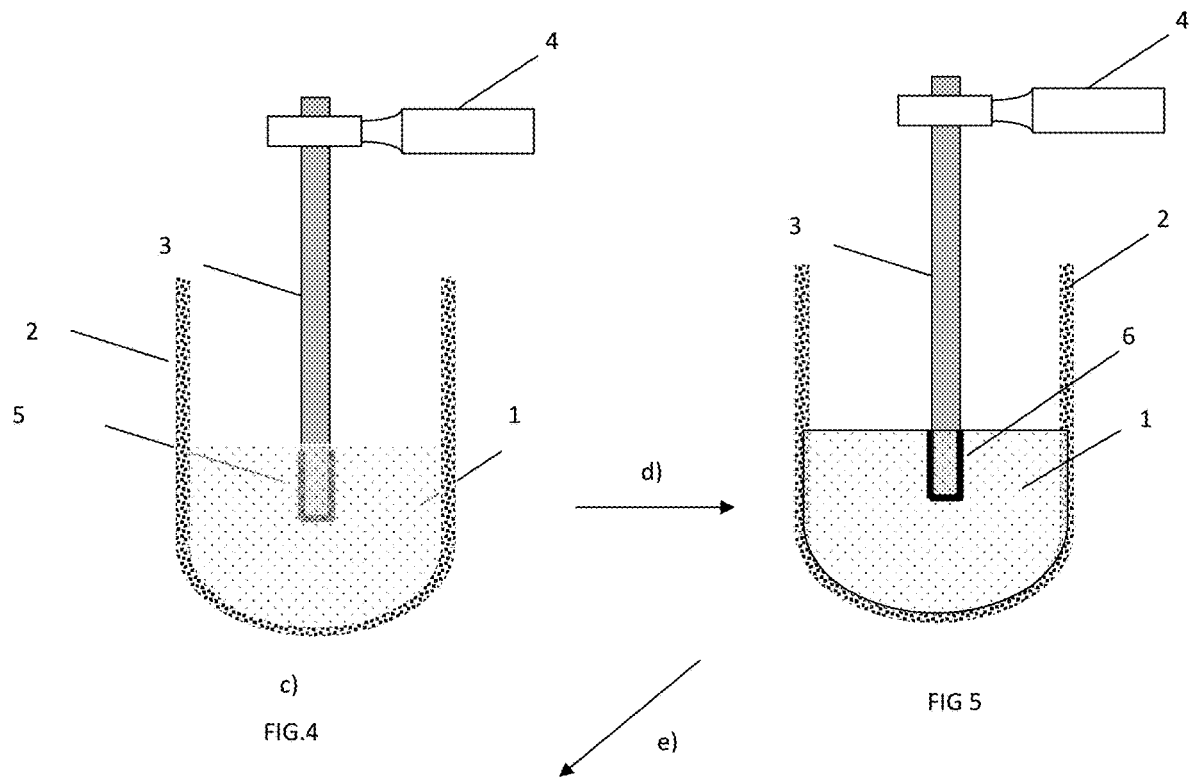
c)
FIG.4
d)
FIG 5
e)
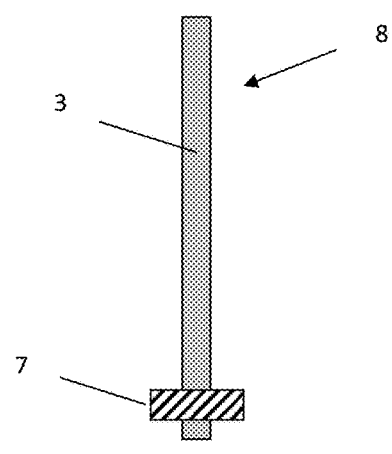
FIG .6

METHOD FOR WETTING A SONOTRODE

CROSS REFERENCE TO RELATED APPLICATIONS

This application is a § 371 National Stage Application of PCT/FR2015/052679, filed Oct. 6, 2015, which claims priority to French Application No. 14/02256 filed Oct. 7, 2014.

BACKGROUND OF THE INVENTION

The present invention relates to a method for using a sonotrode, particularly a sonotrode made of ceramic, in liquid aluminium and/or magnesium. According to a second aspect, the present invention relates to an insonification device comprising said sonotrode.

DESCRIPTION OF RELATED ART

In the field of casting of metals and more particularly of liquid aluminium, it is of the utmost importance to control the quality of the liquid metal, for example by determining the inclusion cleanliness. Indeed, thereupon depend the quality and rejection rate of sheets prepared from liquid aluminium for the manufacture of items, in particular closed receptacles such as beverage or aerosol cans. If applicable, it is necessary to apply suitable treatments such as degassing, filtration with a view to reducing the number of inclusions, etc., in order to enhance the quality of the metal before performing casting.

Sonic methods for the measurement and treatment of liquid metals with a low melting point (Ga, Sn, Pb, Zn, etc.) have been developed since the 1960s. These methods use metal waveguides coupled with liquid metals for emitting and receiving waves, by means of the wetting of the waveguides obtained respectively by the metals to be analysed.

In-line non-destructive testing in liquid aluminium and the treatment thereof encounters the very reactive nature thereof. Indeed, the wetting by liquid aluminium of metals used as sonic waveguides (steels, titanium, etc.) results in the dissolution of these metals, such that measurements made in liquid aluminium are not reliable in the long term.

In addition, the wetting, even in this case, is not perfect, and methods have been developed to enhance same. Evidence of this is particularly found in the patent EP0035545B1, subject to a priority date of 1979, held by "Reynolds Metal Company" claiming the vapour phase deposition of an aluminium film on a titanium sonotrode. However, in fact, even in such a design, the wetting quality varies during use due to the reaction of the waveguide material with the liquid aluminium.

Moreover, the use of refractory ceramic waveguides is not optimal due to the lack of wetting of ceramics by aluminium preventing satisfactory coupling between the sonotrode and the liquid metal. A wetting interface between the ceramic and aluminium could be created by prior chemical deposition of a metal on the waveguide but this deposition method is costly and the deposition in question short-lived.

SUMMARY

One of the aims of the invention is that of developing a stable interface between the waveguide and the liquid aluminium, preventing any dissolution of the constituent material of the waveguide and not requiring the performance of interface deposition. To this end, the present invention relates to a method for using a sonotrode comprising the following steps:

a) Providing a first bath of a liquid metal comprising aluminium with a content X and magnesium with a content Y, the magnesium content Y being different to zero, b) Immersing at least partially a sonotrode formed from a material inert to liquid aluminium, in the first liquid metal bath, and c) Applying power ultrasounds to the sonotrode so as to excite the liquid metal until wetting of the sonotrode by the liquid metal is obtained.

d) Cooling the first metal of the first bath until solidification of the first liquid metal around the sonotrode is obtained, generating an intimate bond between the sonotrode and the solidified first liquid metal having a bonding strength substantially equal to that of brazing between two metals.

e) Machining the solidified first metal in the form of a flange configured for the attachment of a mechanical amplifier and/or of a transducer.

BRIEF DESCRIPTION OF THE DRAWINGS

FIGS. 1-8 depict embodiments of the disclosure.

DETAILED DESCRIPTION OF A PREFERRED EMBODIMENT

Figure 1:
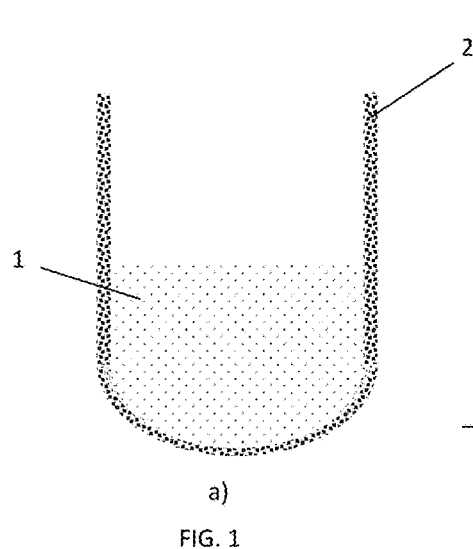

As such, by means of this method, the sonotrode, once it has emerged from the first liquid metal bath, exhibited the presence of a stable layer of aluminium and/or magnesium, i.e. which cannot be peeled off as is usually the case for a ceramic merely immersed in liquid aluminium, demonstrating the existence of wetting of the sonotrode.

Furthermore, the sonotrode having undergone this treatment and subsequently used in liquid aluminium exhibited the capacity thereof to transmit and receive low-power ultrasonic waves in the MHz range, commonly referred to as measurement ultrasounds, also proving that wetting had been obtained.

Preferably, step a) consists of providing a first bath of liquid metal comprising magnesium with a content Y greater than or equal to 0.05%, preferably a content Y greater than 0.5%, and more preferably a content Y greater than or equal to 0.7% by weight.

Indeed, associating a small quantity of magnesium with liquid aluminium makes it possible to obtain satisfactory wetting of the sonotrode by the aluminium. The wetting is obtained all the more quickly as the magnesium content of the liquid metal is high. The excitation time is particularly maintained for several minutes for magnesium contents less than 1% and less than one minute for a presence of Mg of approximately 5%.

According to one option, step a) consists of providing a first liquid metal bath wherein the liquid aluminium content X is zero. In this alternative embodiment, the sonotrode is then wetted by magnesium. As such, the method offers an alternative to the method for wetting a sonotrode by magnesium, which is generally obtained using a sonotrode made of a titanium or steel material. This broadens the sonotrode materials that can be envisaged for wetting with magnesium and the fields of application.

Advantageously, the sonotrode immersed in step b) is formed from a silicon nitride or silicon oxynitride ceramic, particularly a SiAlON. It is understood in the present document that the term SiAlON comes from the acronym "Silicon-Aluminium-Oxygen-Nitride", defining a family of refractory ceramics based on silicon, aluminium, nitrogen and oxygen, also defined as silicon and aluminium oxynitrides. Obtaining wetting with SiAlON, a material known to be inert with respect to liquid aluminium and widely used in the aluminium industry, is all the more surprising as even after extended contact times, aluminium does not adhere to SiAlON tubes used as immersion heater cladding. The proof is that the aluminium layer remaining after the emersion of the SiAlON cladding is readily peeled off.

According to one arrangement, step c) for applying power ultrasounds consists of applying low-frequency ultrasounds. Preferably, the frequency used is between 10 and 40 kHz. The power of the ultrasounds applied is for example between 50 and 150 W. These frequencies are typically suitable for exciting the sonotrode and the liquid aluminium. Further powers can obviously be used provided that they allow the generation of cavitation in the liquid metal in a time compatible with industrial constraints, typically in a few minutes.

For example, for a magnesium content Y of 2.5% by weight, with ultrasounds of a frequency of approximately 20 KHz and a power of 150 W, the excitation time required is less than 10 minutes to obtain wetting of the sonotrode.

According to one option, step a) comprises the provision of a first liquid metal bath comprising aluminium with a content X different to zero such that the first bath comprises a first liquid aluminium alloy.

The method comprises, after step c), a step d) for cooling the first liquid aluminium alloy of the first bath until the solidification of the first aluminium alloy around the sonotrode is obtained, generating an intimate bond between the sonotrode and the solidified first aluminium alloy.

By means of this method, the sonotrode is intimately bonded with a solidified aluminium alloy, with similar properties to those obtained upon brazing between two metals. A polished section of the interface obtained using this method between the sonotrode bonded to the aluminium, observed by scanning electron microscopy (SEM) indeed shows sealing with a perfect bond, without any decohesion and a continuity between the two materials so as to enable optimal mechanical coupling between the aluminium and the sonotrode.

As such, the intimate bond between the sonotrode and the solidified first aluminium alloy has a bonding strength at least substantially equal to that of brazing between two metals.

Again according to this option, the method comprises a step e), carried out after step d), for machining the solidified first aluminium alloy in the form of a flange configured for the attachment of a mechanical amplifier and/or of a transducer. Obviously, this step e) for machining the solidified aluminium is carried out after the release thereof from the crucible. This design makes it possible to obtain mechanical coupling without decohesion despite the transmission of power ultrasounds for several hours continuously. No sign of decoupling appears between the transducer screwed to the flange and the sonotrode. This design makes it possible to greatly enhance the quality of the assembly formed conventionally between the sonotrode and the transducer using a metal flange merely clamped on the sonotrode. Indeed, this assembly according to the prior art is unsuitable for transmitting high powers for times greater than a few minutes.

According to one alternative embodiment, the method comprises after step e), steps for f) Immersing the other end of the sonotrode (3) and wetting in the first bath of liquid metal (1) said sonotrode (3) as in step c), g) Providing a second bath of a second liquid aluminium alloy, h) Immersing at least partially the sonotrode in the second bath of the second liquid aluminium alloy, and i) Applying power ultrasounds to the sonotrode to regenerate the wetting j) Applying power or measurement ultrasounds to the sonotrode The sonotrode initially wetted in the first aluminium alloy is indeed reusable in another aluminium bath separate from the first bath. In this case, it is preferable to reapply power ultrasounds to the sonotrode to reactivate the wetting. Indeed, emerging the wetted sonotrode from the first bath in a non-anhydrous atmosphere would generate the formation of an oxide on the surface, impeding ultrasound transmission. Applying power ultrasounds in the second bath then enables the regeneration of the wetting, even in the absence of magnesium therein. In this alternative embodiment, the flange suitable for attaching the transducer to the sonotrode can be formed according to steps d) and e) of the method described above.

In this case, the second liquid aluminium alloy provided in step g) comprises magnesium with a content Y' between 0 and 0.7% by weight.

According to one option, the second liquid aluminium alloy of the second bath provided in step g) is formed from a liquid AlSiMg alloy, the liquid AlSiMg alloy comprising Si with a content of 0.5 to 7% by weight and Mg with a content Y' of 0 to 0.7% by weight of Mg. It is as such possible to use a sonotrode wetted by means of the invention to transmit durably and effectively power ultrasounds for the treatment of any type of liquid aluminium alloy or measurement ultrasounds for non-destructive testing of the alloy.

According to a further alternative embodiment, the second bath comprises any type of liquid aluminium alloy, such as for example of the type AlCuMg.

When the liquid aluminium content X of the first liquid metal bath is zero, the wetting of the sonotrode is then performed by magnesium which however enables subsequent use for carrying ultrasounds in a second aluminium alloy bath.

The ultrasounds applied in step i) of the method, when the second aluminium alloy bath differs from the first liquid metal bath, particularly have a vibration frequency between 10 and 40 kHz, preferably approximately 20 kHz, and for example with a power between 50 and 150 W, preferably approximately 150 W, for a time of a few minutes, and preferably approximately 10 minutes.

According to a second aspect, the invention relates to an insonification device comprising at least a sonotrode made of ceramic, formed from silicon nitride or silicon oxynitride, such as a SiAlON, and a flange made of aluminium alloy attached by an intimate bond to the sonotrode. This device provides durable mechanical coupling between a transducer and the sonotrode and means that liquid aluminium quality measurements can be envisaged. Moreover, this device can be used in combination with the method for wetting the sonotrode made of SiAlON by liquid aluminium so as to enhance the reliability of the non-destructive testing measurements of the liquid aluminium, such as the detection of inclusions, Doppler sonic velocimetry, hydrophony in the liquid aluminium.

Further aspects, aims and advantages of the present invention will emerge more clearly on reading the following description of an embodiment thereof, given by way of non-limiting example and with reference to the appended figures. The figures do not necessarily observe the scale of the elements represented so as to improve the legibility thereof. Hereinafter in the description, for the purposes of simplification, identical, similar or equivalent elements of the various embodiments bear the same reference numbers.

Figure 2:
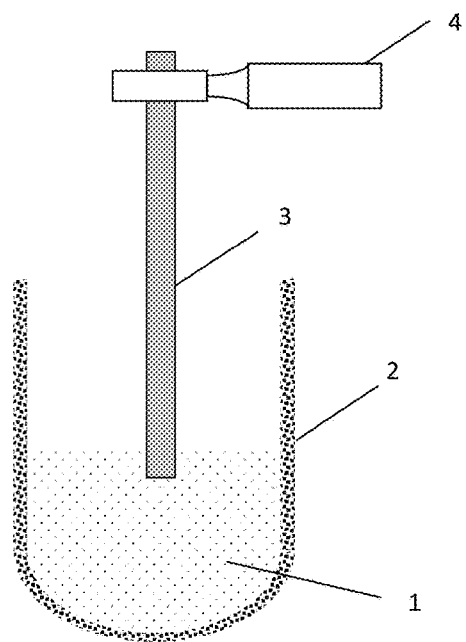
Figure 3:
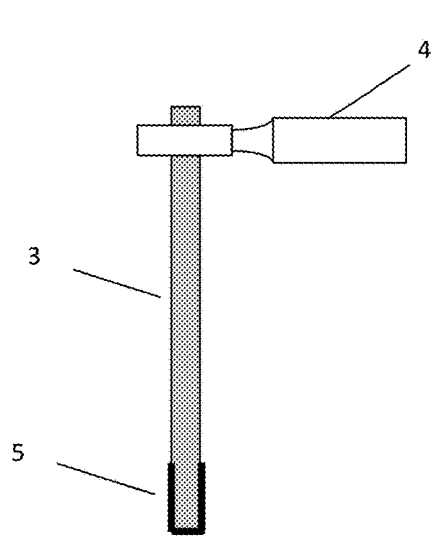

FIGS. 1 to 3 are an illustration of the schematic diagram of the method for using a sonotrode according to one embodiment of the invention.

FIGS. 4 to 6 are an illustration of the schematic diagram of the formation of an intimate bond according to one embodiment of the invention.

Figure 7:
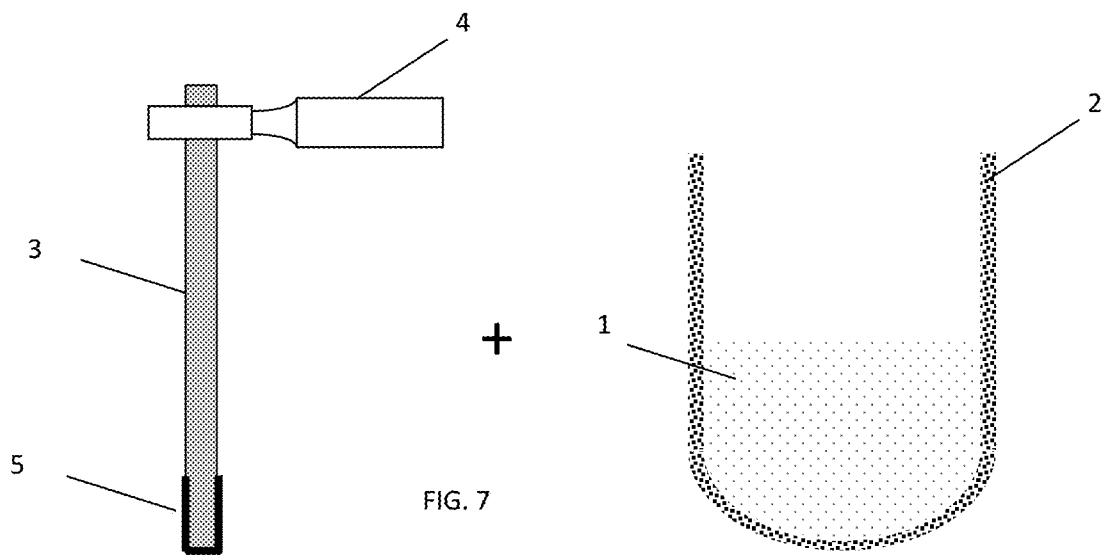
Figure 8:
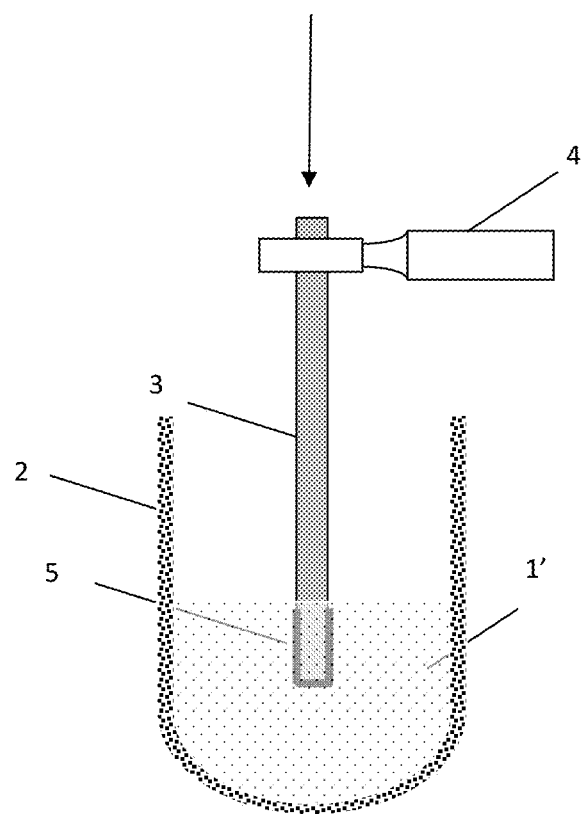

FIGS. 7 to 8 are an illustration of the schematic diagram of a further use of the sonotrode wetted according to one embodiment of the invention.

As illustrated in FIG. 1, a first bath of a liquid metal 1 is prepared in a receptacle 2 such as a crucible. The liquid metal 1 particularly comprises a non-zero content X of liquid aluminium (main component) and a content Y of magnesium of approximately 0.7% by weight according to step a) of the method. A sonotrode 3 made of SiAlON ceramic, which is refractory and inert to liquid aluminium, is then immersed partially in the first bath of liquid metal 1 (step b) FIG. 2). Power ultrasounds are applied via a transducer 4 or a transducer-amplifier assembly to the sonotrode 3 so as to excite same (step c). The power ultrasounds applied are low-frequency ultrasounds, of the order of 20 kHz with a power of 150 W. After a few minutes of this treatment, wetting 5 of the sonotrode 3 is formed, a layer or film of aluminium not suitable for being readily peeled off is indeed found on the surface of the sonotrode 3 (FIG. 3). Further so-called "low-frequency" vibration frequencies particularly between 10 and 40 kHz can be used to excite the liquid metal 1 via the sonotrode 3. Similarly, further power values can be envisaged insofar as they are sufficient to generate the cavitation phenomenon in the liquid metal in a time compatible with industrial methods so as to obtain wetting rapidly.

According to one alternative embodiment not illustrated, the magnesium content Y in the liquid metal 1 is 0.05, or 0.5% by weight. The sonic treatment time for obtaining wetting is thereby extended compared to that obtained for a magnesium content Y of 0.7% by weight.

According to one alternative, the same treatment time for obtaining wetting as that obtained with a magnesium content Y of 0.7% by weight is carried out due to the increase in the ultrasound power.

Moreover, according to a further alternative embodiment, any sonotrode 3 consisting of a material inert to liquid aluminium such as a refractory ceramic of the silicon nitride or silicon oxynitride family is wetted by liquid aluminium by means of this method.

According to a further alternative embodiment not illustrated, the aluminium content X of the first bath 1 is zero. In this case, the wetting of the sonotrode 3 is obtained with magnesium the content Y whereof is close to 100% by weight. This sonotrode 3 wetted in this way is then immersed in a second bath of a second liquid aluminium alloy in order to be subsequently suitable for carrying ultrasounds without loss of power for a long period.

According to one option illustrated in FIGS. 4 to 6, the first bath comprising the first liquid aluminium alloy 1, wherein the sonotrode 3 is wetted by applying power ultrasounds (FIG. 4—step c), is allowed to return to ambient temperature (FIG. 5—step d). Once cooled, the first aluminium alloy 1 is solidified around the sonotrode 3, generating an intimate bond 6 between the sonotrode 3 and the solidified alloy 1 (seen in FIG. 5). The intimate bond 6 corresponds to sealing with a perfect bond, without any decohesion and metallurgical continuity between the ceramic and the first aluminium alloy. Then, the sonotrode 3 intimately bonded with the first aluminium alloy 1 is released from the crucible 2 and the solidified alloy 1 is machined by turning and drilling so as to form a cylindrical flange 7 intimately bonded with the ceramic (FIG. 6, step e). The intimate bond 6 between aluminium and SiAlON is formed with similar properties to those obtained upon brazing between two metals. An insonification device 8 is thereby obtained, it enables optimal mechanical coupling between aluminium and the sonotrode 3.

Obviously, this method can be implemented using alloys of aluminium and magnesium of different compositions, with or without silicon and particularly using an alloy including copper. According to one option illustrated in FIGS. 7 and 8, the sonotrode 3 wetted by liquid aluminium, is removed from the first bath 1 (step f, FIG. 7) to be partially immersed in a second bath of liquid aluminium alloy 1' (step g, h, FIG. 8). Ultrasounds are applied to the sonotrode 3 with a vibration frequency of 20 kHz and a power of approximately 150 W so as to regenerate the wetting 5 (step i) even in the absence of magnesium in the second liquid aluminium alloy 1'. The second liquid aluminium alloy 1' is indeed formed from AlSiMg with a content between 0.5 and 7% by weight of Si and a content Y of 0% to 0.7% by weight of Mg. The sonotrode 3 obtained thereby can then be reused for effectively transmitting the power, or measurement, ultrasounds (with frequency of 100 kHz for example) in the second liquid aluminium alloy 1'.

According to one option not illustrated, the flange 7 in an intimate bond 6 with the sonotrode 3 following step f), FIG. 6, of the method is subsequently used for attaching a transducer 4. The sonotrode 3 attached in this way to the transducer 4 is then wetted in a bath of an aluminium alloy as described above. The ultrasounds emitted by the transducer 4 are then transmitted via the flange 7 to the wetted sonotrode 3 which in turn transmits the ultrasounds to the bath of aluminium alloy with a view to performing tests or treatments of the liquid aluminium for quality casting.

As such, the present invention relates to a method for using a sonotrode 3 by wetting obtained using aluminium or magnesium, which is inexpensive and simple to carry out. The invention also relates to the formation of an intimate bond 6 between the material of the sonotrode and a solidified aluminium alloy 1' which is very simple to implement and suitable for producing a flange 7 perfectly sealed to the sonotrode 3, and suitable for long-term use particularly for transmitting measurement or power ultrasounds.

It is obvious that the invention is not limited to the embodiment described above by way of example but that it includes any technical equivalents and the alternative embodiments of the means described as well as the combinations thereof.

The invention claimed is:
1. A method for using a sonotrode comprising:
  a) providing a first bath of a liquid metal comprising aluminium with a content X and magnesium with a content Y, the magnesium content Y being different from zero,
  b) immersing at least partially a sonotrode formed from a material inert to liquid aluminium, in the first bath of liquid metal, c) applying power ultrasounds to the sonotrode so as to excite the liquid metal until wetting of the sonotrode by the liquid metal is obtained,
d) cooling the first liquid metal of the first bath until solidification of the first liquid metal around the sonotrode is obtained, generating an intimate bond between the sonotrode and the solidified first liquid metal,
e) machining the solidified first metal in the form of a flange configured for attachment of a mechanical amplifier and/or of a transducer,
f) immersing the other end of the sonotrode and wetting in the first bath of liquid metal said sonotrode as in c),
g) providing a second bath of a second liquid aluminium alloy,
h) immersing at least partially the sonotrode in the second bath of the second liquid aluminium alloy,
i) applying power ultrasounds to the sonotrode to regenerate the wetting,
j) applying power or measurement ultrasounds to the sonotrode.

2. The method according to claim 1, wherein the second liquid aluminium alloy provided in g) comprises magnesium with a content Y' between 0 and 0.7% by weight.

3. The method according to claim 1, wherein the second liquid aluminium alloy of the second bath provided in g) is formed from a liquid AlSiMg alloy, the liquid AlSiMg alloy comprising Si with a content of 0.5 to 7% by weight and Mg with a content Y' of 0 to 0.7% by weight of Mg.

4. The method according to claim 1, wherein in i), the power ultrasounds have a frequency between 10 and 40 kHz.

5. The method according to claim 1, wherein a) comprises providing a first bath of liquid metal comprising magnesium with a content Y greater than or equal to 0.05% by weight.

6. The method according to claim 1, wherein a) comprises providing a first bath of liquid metal comprising magnesium with a content Y greater than or equal to 0.5% by weight.

7. The method according to claim 1, wherein a) comprises providing a first bath of liquid metal comprising magnesium with a content Y greater than or equal to 0.7% by weight.

8. The method according to claim 1, wherein the sonotrode immersed in b) is formed from a silicon nitride or silicon oxynitride ceramic.

9. The method according to claim 8, wherein the sonotrode immersed in b) is formed from a SiAlON.

10. The method according to claim 1, wherein the intimate bond between the sonotrode and the solidified first liquid metal does not have any decohesion and demonstrates a continuity between the sonotrode and the solidified first liquid metal.

* * * * *